(12) United States Patent
Takenaka et al.

(10) Patent No.: US 8,404,480 B2
(45) Date of Patent: Mar. 26, 2013

(54) MICROORGANISM TESTING DEVICE AND MICROORGANISM TESTING CHIP

(75) Inventors: Kei Takenaka, Kashiwa (JP); Yasuhiko Sasaki, Tsuchiura (JP); Hideki Nakamoto, Tokai (JP); Kazuo Takei, Tokai (JP); Masahiro Kurihara, Yokohama (JP); Yuusuke Watanabe, Hitachi (JP); Hisao Saito, Matsudo (JP)

(73) Assignee: Hitachi Engineering & Services Co., Ltd., Ibaraki (JP)

( * ) Notice: Subject to any disclaimer, the term of this patent is extended or adjusted under 35 U.S.C. 154(b) by 541 days.

(21) Appl. No.: 12/575,489

(22) Filed: Oct. 8, 2009

(65) Prior Publication Data

US 2010/0093072 A1    Apr. 15, 2010

(30) Foreign Application Priority Data

Oct. 9, 2008    (JP) .................................. 2008-263055

(51) Int. Cl.
  *C12M 1/34*    (2006.01)
  *G01N 21/03*    (2006.01)
(52) U.S. Cl. ............... 435/288.7; 435/288.5; 435/287.3; 422/82.08; 422/82.09
(58) Field of Classification Search ............... 435/288.5, 435/288.7
  See application file for complete search history.

(56) References Cited

U.S. PATENT DOCUMENTS

| 6,316,781 B1 * | 11/2001 | Nagle et al. ................... 250/573 |
| 2008/0153153 A1 | 6/2008 | Takenaka et al. |
| 2009/0291488 A1 | 11/2009 | Takenaka et al. |

FOREIGN PATENT DOCUMENTS

JP    2005-245317    9/2005

OTHER PUBLICATIONS

Carsten Buhlmann et al.; A New Tool for Routine Testing of Cellular Protein Expression: Integration of Cell Staining and Analysis of Protein Expression on a Microfluidic Chip-Based System; Jornal of Biomolecular Techniques, Jun. 2003; p. 119-127; vol. 14, Issue 2.; Waldbronn, Germany Carsten_Buhlmann@Agilent.com.

* cited by examiner

*Primary Examiner* — William H Beisner
(74) *Attorney, Agent, or Firm* — Antonelli, Terry, Stout & Kraus, LLP.

(57) ABSTRACT

Provided are a microorganism testing chip capable of suppressing self-fluorescence and enhancing mass productivity, and a microorganism testing device using the same. The microorganism testing chip includes a main body and a fungus body detection unit mounted on the main body. The main body has a detection window frame portion which is a through-hole or a pass-through groove. The fungus body detection unit is disposed to cover the detection window frame portion and has a fungus body detection flow path connected to flow paths provided in the main body. The fungus body detection unit includes a cover member and a flow path member, and is formed by attaching these two members to each other. The flow path member has a groove. By attaching the two members to each other, the groove of the flow path member serves as the fungus body detection flow path.

18 Claims, 7 Drawing Sheets

MICROORGANISM TESTING DEVICE AND MICROORGANISM TESTING CHIP

BACKGROUND OF THE INVENTION

1. Field of the Invention

The present invention relates to a microorganism testing device and a microorganism testing chip for measuring microorganisms.

2. Description of the Related Art

Conventionally, various measuring devices for quick and simple measurement of the number of viable bacteria have been known. Some of such devices for measuring the number of bacteria use a fluorescence flow cytometry method. The fluorescence flow cytometry method is a particle measuring method in which specimens dyed with a fluorochrome are directly measured one by one when a fluid including the specimens passes through a flow path having a small diameter. In the fluorescence flow cytometry method, in order to prevent elements in the specimens from adhering to the wall of the flow path, sheath liquid is provided to surround the flow including the specimens. These two liquids are formed into a laminar flow, and the specimen flow is focused to have its diameter narrowed down using the pressure difference between the two liquids. Further, in the fluorescence flow cytometry method, in order to cut down the cost and eliminate cleaning processing, a disposable chip is used in some cases as a flow path portion used for measuring the number of specimens. Examples using a disposable chip in this way are described in Japanese Patent Application Publication No. 2005-245317 and Journal of Biomolecular Techniques, Vol. 14, Issue 2, pp. 119-127.

SUMMARY OF THE INVENTION

It is generally known that a disposable microorganism testing chip is used in optical measurement of specimens dyed with a fluorochrome. There are some imperatives associated with the use of the disposable microorganism testing chip. First, the microorganism testing chip must be inexpensive. To fabricate the microorganism testing chip at low cost, the material cost and processing cost of the microorganism testing chip must be low. Next, it is necessary to reduce the occurrence of self-fluorescence caused by induced emission and fluorescence from the microorganism testing chip itself.

To fabricate a microorganism testing chip having low self-fluorescence, materials having low induced emission and self-fluorescence can be employed.

Glass and quartz are materials having lowest self-fluorescence and are more excellent than other materials in optical performances such as profile irregularity, refractive index, and birefringence index. That is why analysis cells of fluorescence spectroscopes are made of glass or quartz. However, glass or quartz cannot be used to form a fine flow path with high precision at low cost. Accordingly, it is preferable to use easily micromachinable resin. Various resin materials suitable for micromachining are known. In particular, polydimethylsiloxane and cyclo olefin polymer are known as materials having low self-fluorescence, and are used in substitution for glass, quartz, or the like in some cases. Polydimethylsiloxane and cyclo olefin polymer are more advantageous in terms of cost and mass productivity than glass and quartz, but have the problems that they are higher in material costs and lower in chemical resistances than other resin materials such as polypropylene and polystyrene.

An object of the present invention is to provide a microorganism testing chip capable of suppressing self-fluorescence and enhancing mass productivity, and a microorganism testing device using the microorganism testing chip.

According to the present invention, a microorganism testing chip includes a main body and a fungus body detection unit mounted on the main body. The main body includes a detection window frame portion which is a through-hole or a pass-through groove. The fungus body detection unit is disposed to cover the detection window frame portion. The fungus body detection unit includes a fungus body detection flow path connected to the flow paths provided in the main body. The fungus body detection unit includes a cover member and a flow path member, and is formed by attaching these two members to each other. The flow path member has a groove. By attaching the two members to each other, the groove of the flow path member serves as the fungus body detection flow path.

The present invention can provide a microorganism testing chip capable of suppressing self-fluorescence and enhancing mass productivity, and a microorganism testing device using the microorganism testing chip.

DESCRIPTION OF THE PREFERRED EMBODIMENTS

Figure 1:
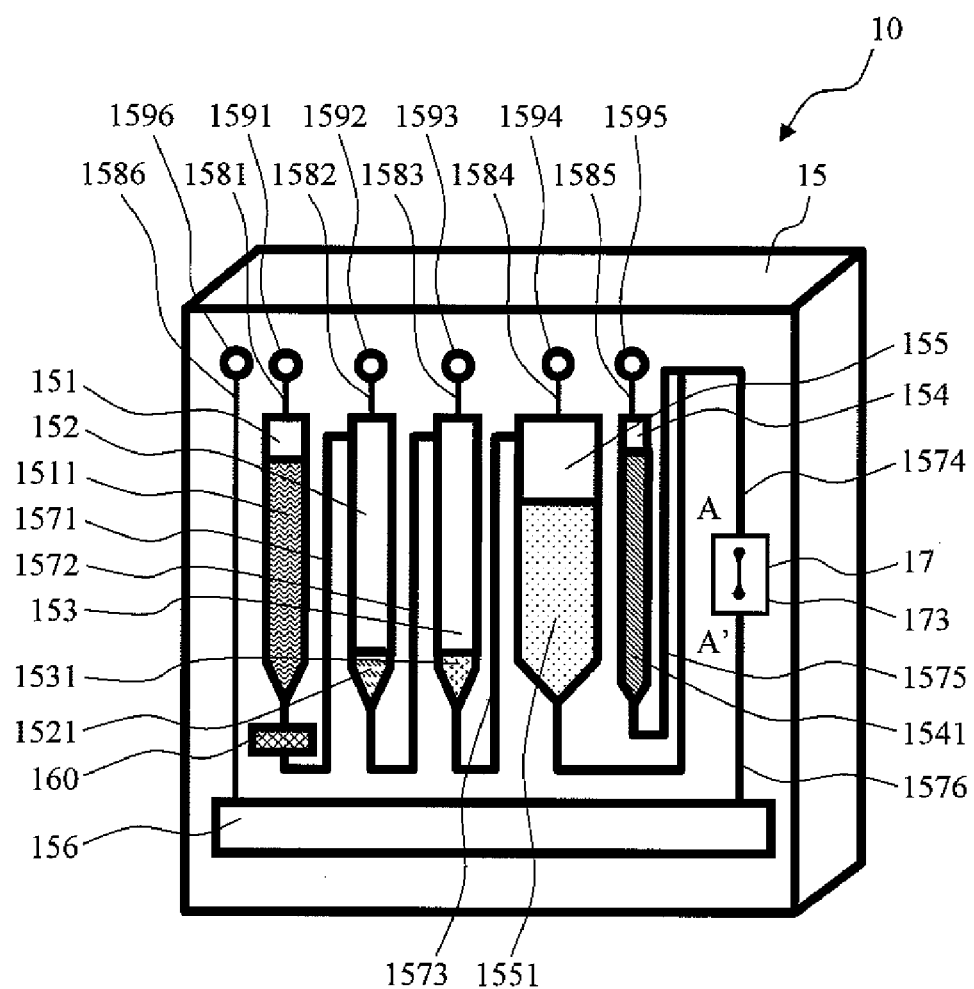
FIG. 1 is a view showing a configuration example of a microorganism testing chip of the present invention.

Hereinafter, an embodiment of the present invention will be described with reference to the drawings. FIG. 1 is a schematic diagram of a microorganism testing chip 10 used in a microorganism testing device of the present invention. First, a configuration of the microorganism testing chip 10 will be described. The microorganism testing chip 10 includes a main body 1 and a fungus body detection unit 17 for detecting a fungus body. In the main body 15, a food residue contained in a specimen is removed and a fungus body is dyed. The fungus body detection unit 17 has a fungus body detection flow path 173 which is irradiated with excitation light from an external light source and used in the observation of fluorescence of microorganisms. Details of the structure of the fungus body detection unit 17 will be described later with reference to FIGS. 2A and 2B. Here, the main body 15 will be described.

The main body 15 includes a specimen container 151 for holding a specimen 1511, a killed bacteria dyeing reagent holding container 152 serving as a reaction container for holding killed bacteria dyeing pigment 1521, an all bacteria dyeing reagent holding container 153 serving as a reaction container for holding all bacteria dyeing pigment 1531, a positioning reagent holding container 154 for holding a positioning reagent 1541, a diluent holding container 155 for holding diluent 1551, a food residue removing portion 160 serving as a filter for removing a food residue contained within the specimen 1511, and a detection liquid waste container 156 for discarding various unnecessary waste liquids which have passed through the fungus body detection flow path 173. The waste liquids discarded to the detection liquid waste container 156 include the specimen 1511, a liquid mixture of the specimen 1511, the killed bacteria dyeing pigment 1521, and the all bacteria dyeing pigment 1531, and the positioning reagent 1541.

The bottom surface of each of these containers 151, 152, 153, 154, and 155 is formed in the shape of a funnel. As shown in FIG. 1, the microorganism testing chip 10 is held upright so that the bottom surfaces of these containers 151, 152, 153, 154, and 155 may be located below.

The main body 15 further includes solution flow paths 1571-1576, ventilation ports 1591-1596, and air flow paths 1581-1586. The solution flow paths 1571 to 1576 connect the specimen container 151, the food residue removing portion 160, the killed bacteria dyeing reagent holding container 152, the all bacteria dyeing reagent holding container 153, and the fungus body detection flow path 173. The specimen 1511 and a liquid mixture flow through the solution flow paths 1571-1576. The pressure through the ventilation ports 1591-1596 causes the specimen 1511 or the liquid mixture in each of the above-described containers to be flowed. The air flow paths 1581-1586 respectively connect the ventilation ports 1591-1596 to the respective containers. From the names of the containers to be connected, the solution flow paths 1571-1576, the ventilation ports 1591-1596, and the air flow paths 1581-1586 are respectively referred to as the flow path 1571 between specimen container and killed bacteria dyeing reagent holding container, the flow path 1572 between killed bacteria dyeing reagent holding container and all bacteria dyeing reagent holding container, the flow path 1573 between all bacteria dyeing reagent holding container and diluent holding container, the flow path 1574 between diluent holding container and fungus body detection flow path, the flow path 1575 between positioning reagent holding container and fungus body detection flow path, the flow path 1576 between fungus body detection flow path and detection liquid waste container, the specimen container ventilation port 1591, the killed bacteria dyeing reagent holding container ventilation port 1592, the all bacteria dyeing reagent holding container ventilation port 1593, the diluent holding container ventilation port 1594, the positioning reagent holding container ventilation port 1595, the detection liquid waste container ventilation port 1596, the specimen container air flow path 1581, the killed bacteria dyeing reagent holding container air flow path 1582, the all bacteria dyeing reagent holding container air flow path 1583, the diluent holding container air flow path 1584, the positioning reagent holding container air flow path 1585, and the detection liquid waste container air flow path 1586.

The specimen container 151, the food residue removing portion 160, the killed bacteria dyeing reagent holding container 152, the all bacteria dyeing reagent holding container 153, the diluent holding container 155, the fungus body detection flow path 173, and the detection liquid waste container 156 are connected in series by the solution flow paths 1571-1574 and 1576. The flow path 1575 between positioning reagent holding container and fungus body detection flow path joins to the flow path 1574 between diluent holding container and fungus body detection flow path.

The solution flow paths 1571-1576 are formed so as to have the depths and widths to be in the range of 10 μm to 3 mm. The air flow paths 1581-1586 are formed so as to have the depths and widths to be in the range of 10 μm to 3 mm. The solution flow paths 1571-1576 are formed so as to have the cross-sectional areas to be larger than those of the air flow paths 1581-1586. A method of fabricating the main body 15 is not particularly described here. As described in Patent Document 1 and Non-Patent Document 1, a method of fabricating a microorganism testing chip is known.

The material for the main body 15 will be described. Since the microorganism testing chip 10 is disposable, the main body 15 is formed from an inexpensive material. The main body 15 has a complicated structure inside. For this reason, the main body 15 is formed from an easily micromachinable material of low processing-cost. Glass and quartz have low self-fluorescence and excellent optical characteristics, but are not easily micromachinable. That is, the micromachining of glass or quartz requires a high processing cost. The main body 15 holds a specimen before treatment and a dyeing reagent inside. Accordingly, the main body 15 is formed from a chemical resistant material. For the above-described reasons, possible materials for the main body 15 include polypropylene, polyethylene terephthalate, poly carbonate, polystyrene, acrylonitrile butadiene styrene resin, polymethacrylic acid methyl ester, and the like. The main body 15 is formed from at least one material selected from these materials.

The killed bacteria dyeing reagent 1521, the all bacteria dyeing reagent 1531, and the positioning reagent 1541 are encapsulated in the microorganism testing chip 10 beforehand. The specimen 1511 is injected into the specimen container 151 from the ventilation port 1591 before testing. The diluent 1551 is injected into the diluent holding container 155 from the ventilation port 1594 before testing.

The specimen 1511 is obtained by stomaching a food to be inspected after adding physiological salt solution which is ten times by mass relative to the food to be inspected. The diluent 1551 is buffer solution such as physiological salt solution, pure water, or phosphate-buffered physiological salt solution primarily. The diluent 1551 is also used as cleaning liquid.

The killed bacteria dyeing reagent 1521 may be, for example, PI (propidium iodide) (0.1 μg/ml to 1 mg/ml). The all bacteria dyeing reagent 1531 may be, for example, DAPI (4',6-diamidine 2'-phenylindole) (1 μg/ml to 1 mg/ml), AO (acridine orange) (1 μg/ml to 1 mg/ml), EB (ethidium bromide) (1 μg/ml to 1 mg/ml), LDS751 (0.1 μg/ml to 1 mg/ml), or the like.

As the positioning reagent 1541, a solution is used which contains a fluorochrome such as PI, DAPI, AO, EB, or LDS751 and fine particles that emit fluorescence at a specific wavelength. The wavelength peak of the positioning reagent 1541 is preferably close to that of the killed bacteria dyeing reagent 1521 or the all bacteria dyeing reagent 1531 in order to use an optical system for detection in common. For example, PI (peak wavelength: 532 nm) may be employed for the positioning reagent 1541 and the killed bacteria dyeing reagent 1521, and LDS751 (peak wavelength: 710 nm) may be employed for the all bacteria dyeing reagent 1531.

Next, a method of flowing a specimen and solutions in the microorganism testing chip 10 will be described. In the measurement of the number of viable bacteria using the microorganism testing chip 10, the positioning of the microorganism testing chip 10, that is, of the fungus body detection flow path 173, is performed first, and then the number of viable bacteria is measured. First, the flow of the positioning reagent 1541 in a positioning step will be described. The microorganism testing chip 10 is held upright as shown in the drawing so that the funnel-shaped bottom surfaces of the containers may be located below. The positioning reagent 1541 is caused to flow into the detection liquid waste container 156 through the fungus body detection flow path 173. The flow path 1575 between positioning reagent holding container and fungus body detection flow path is formed so as to have its highest point located higher than the water level of the positioning reagent 1541. Thus, as long as the positioning reagent holding container ventilation port 1595 and the detection liquid waste container ventilation port 1596 are closed, the positioning reagent 1541 held in the positioning reagent holding container 154 does not flow to the detection liquid waste container ventilation port 1596.

Figure 3:
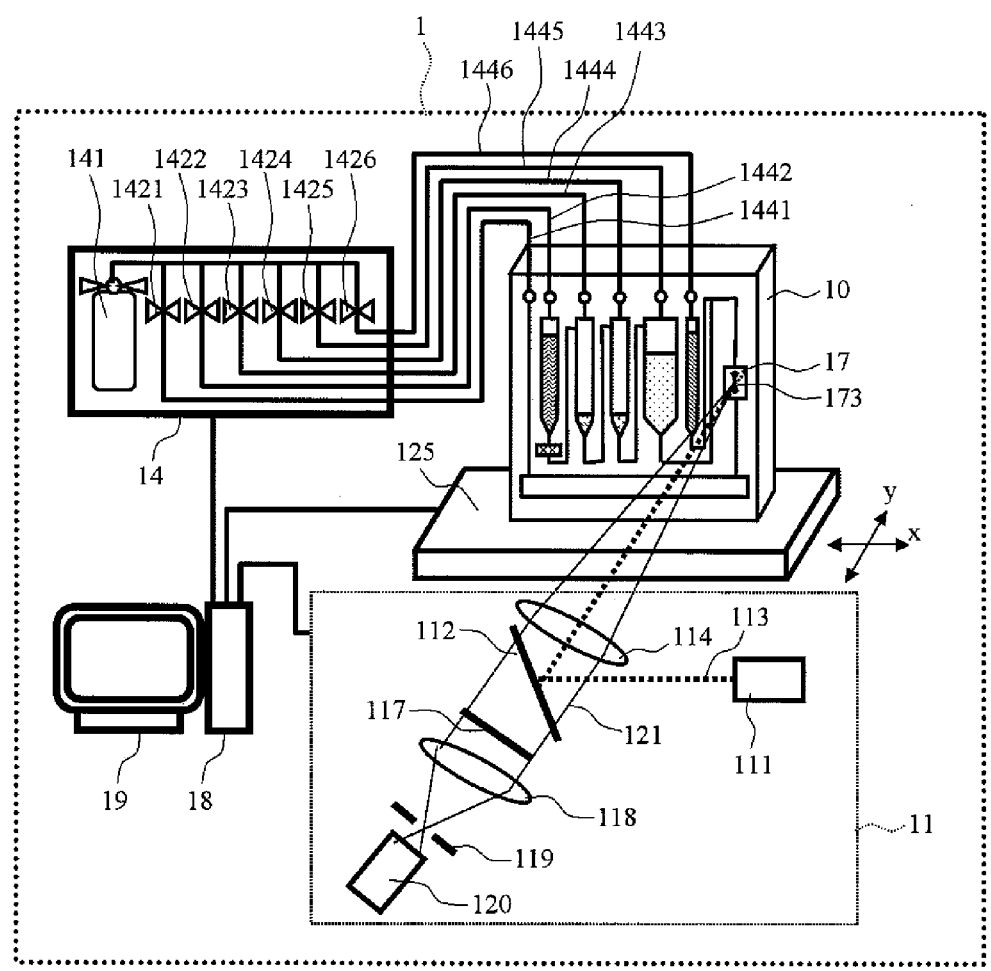
FIG. 3 is a view showing a configuration example of a microorganism testing device of the present invention.

Accordingly, pressure is applied from a pressure supply device 14 (FIG. 3) through the positioning reagent holding container ventilation port 1595 to increase the air pressure in the positioning reagent holding container 154. At the same time, the detection liquid waste container 156 is opened to the atmosphere through the detection liquid waste container ventilation port 1596. The positioning reagent 1541 enters the detection liquid waste container 156 through the flow path 1575 between positioning reagent holding container and fungus body detection flow path and the fungus body detection flow path 173 by the pressure difference. The fungus body detection flow path 173 is irradiated with excitation light from the detection device 11 (FIG. 3). Thus, the positioning reagent 1541 emits fluorescence when passing through the fungus body detection flow path 173. This fluorescence is detected by the detection device 11 (FIG. 3). The position of the microorganism testing chip 10 is adjusted so that the fluorescence detected by the detection device 11 (FIG. 3) may become the maximum. Part of the diluent 1551 is caused to flow into the fungus body detection flow path 173 after the positioning. This cleans the fungus body detection flow path 173 and removes the positioning reagent 1541 remaining in the fungus body detection flow path 173.

Next, the flow of each of the liquids in the step of measuring the number of viable bacteria will be described.

1. The step of flowing the specimen 1511 into the killed bacteria dyeing reagent holding container 152:

The flow path 1571 between specimen container and killed bacteria dyeing reagent holding container is formed so as to have its highest point located higher than the water level of the specimen 1511 held in the specimen container 151. Thus, as long as the specimen container ventilation port 1591 and the killed bacteria dyeing reagent holding container ventilation port 1592 are closed, the specimen 1511 held in the specimen container 151 does not flow into the killed bacteria dyeing reagent holding container 152. Pressure is applied from the pressure supply device 14 (FIG. 3) through the ventilation port 1591 to increase the air pressure in the specimen container 151. At the same time, the killed bacteria dyeing reagent holding container 152 is opened to the atmosphere through the killed bacteria dyeing reagent holding container ventilation port 1592. The specimen 1511 enters the killed bacteria dyeing reagent holding container 152 from the specimen container 151 through the food residue removing portion 160 by the pressure difference and then mixes with the killed bacteria dyeing reagent 1521. When the specimen 1511 passes through the food residue removing portion 160, a food residue in the specimen 1511 is removed by the food residue removing portion 160. Killed bacteria in the specimen 1511 are dyed with the killed bacteria dyeing reagent 1521. On the other hand, the killed bacteria dyeing reagent 1521 does not pass through cell membranes of viable bacteria. Accordingly, viable bacteria in the specimen 1511 are not dyed.

The volume of the killed bacteria dyeing reagent holding container 152 is larger than the total volume of the specimen 1511 and the killed bacteria dyeing reagent 1521. The flow path 1572 between killed bacteria dyeing reagent holding container and all bacteria dyeing reagent holding container is formed so as to have its highest point located higher than the water level of the mixture of the two liquids held in the killed bacteria dyeing reagent holding container 152. The water level of the mixture of the two liquids does not exceed the highest point of the flow path 1572 between killed bacteria dyeing reagent holding container and all bacteria dyeing reagent holding container. Further, the air in the killed bacteria dyeing reagent holding container 152 is discharged to the outside through the killed bacteria dyeing reagent holding container ventilation port 1592. Since the air pressure of the killed bacteria dyeing reagent holding container 152 is equal to the atmospheric pressure, the mixture of the two liquids is not pushed out to the all bacteria dyeing reagent holding container 153, and can be held in the killed bacteria dyeing reagent holding container 152 during the time required for the reaction. Similarly, the all bacteria dyeing reagent 1531 is held in the all bacteria dyeing reagent holding container 153. That is, the all bacteria dyeing reagent 1531 is not pushed out to the diluent holding container 155, and is also not caused to flow backward to the killed bacteria dyeing reagent holding container 152.

At this time, in order to prevent the liquid mixture from flowing into the all bacteria dyeing reagent holding container 153, pressure may be applied from the pressure supply device through the ventilation ports 1593-1596 to increase the air pressures in the all bacteria dyeing reagent holding container 153, the diluent holding container 155, the positioning reagent holding container 155, and the detection liquid waste container 156 to air pressures lower than the air pressure of the specimen container 151.

It should be noted that the temperature of the microorganism testing chip 10 is preferably kept constant during dyeing to reduce the influence of temperature change on dyeing.

2. The step of flowing the liquid mixture of the specimen 1511 and the killed bacteria dyeing reagent 1521 into the all bacteria dyeing reagent holding container 153:

Pressure is applied from the pressure supply device 14 (FIG. 3) through the ventilation port 1592 to increase the air pressure in the killed bacteria dyeing reagent holding container 152. At the same time, the all bacteria dyeing reagent holding container 153 is opened to the atmosphere through the all bacteria dyeing reagent holding container ventilation port 1593. The liquid mixture of the specimen 1511 and the killed bacteria dyeing reagent 1521 enters the all bacteria dyeing reagent holding container 153 from the killed bacteria dyeing reagent holding container 152 by the pressure difference and then mixes with the all bacteria dyeing reagent 1531. Killed and viable bacteria in the specimen 1511 are dyed with the all bacteria dyeing reagent 1531.

The volume of the all bacteria dyeing reagent holding container 153 is larger than the total volume of the specimen 1511, the killed bacteria dyeing reagent 1521, and the all bacteria dyeing reagent 1531. The flow path 1573 between all bacteria dyeing reagent holding container and diluent holding container is formed so as to have its highest point located higher than the water level of the mixture of the three liquids held in the all bacteria dyeing reagent holding container 153. Since the air pressure of the all bacteria dyeing reagent holding container 153 is equal to the atmospheric pressure, the mixture of the three liquids is not pushed out to the diluent holding container 155 and can be held in the all bacteria dyeing reagent holding container 153 during the time required for the reaction.

3. The step of flowing the liquid mixture of the specimen 1511, the killed bacteria dyeing reagent 1521, and the all bacteria dyeing reagent 1531 into the diluent holding container 155:

Pressure is applied from the pressure supply device 14 (FIG. 3) through the ventilation port 1593 to increase the air pressure in the all bacteria dyeing reagent holding container 153. At the same time, the diluent holding container 155 is opened to the atmosphere through the diluent holding container ventilation port 1594. The liquid mixture of the specimen 1511, the killed bacteria dyeing reagent 1521, and the all bacteria dyeing reagent 1531 enters the diluent holding container 155 from the all bacteria dyeing reagent holding container 153 by the pressure difference and then mixes with the diluent 1551. This reduces the concentration of uncombined dye (the killed bacteria dyeing reagent 1521 and the all bacteria dyeing reagent 1531 which do not dye microorganisms) which is contained in the liquid mixture. The reduction of concentration of uncombined dye makes it possible to reduce the intensity of fluorescence emitted by uncombined dye which causes noise at the time of detection.

The volume of the diluent holding container 155 is larger than the total volume of the specimen 1511, the killed bacteria dyeing reagent 1521, the all bacteria dyeing reagent 1531, and the diluent 1551. The flow path 1574 between diluent holding container and fungus body detection flow path is formed so as to have its highest point located higher than the water level of the mixture of the four liquids. Since the air pressure of the diluent holding container 155 is equal to the atmospheric pressure, the mixture of the four liquids is not pushed out to the detection liquid waste container 156 and can be held in the diluent holding container 155.

4. The step of flowing the liquid mixture of the specimen 1511, the killed bacteria dyeing reagent 1521, the all bacteria dyeing reagent 1531, and the diluent 1551 into the fungus body detection flow path 173:

Pressure is applied from the pressure supply device 14 (FIG. 3) through the ventilation port 1594 to increase the air pressure in the diluent holding container 155. At the same time, the detection liquid waste container 156 is opened to the atmosphere through the detection liquid waste container ventilation port 1596. The diluted liquid mixture enters the detection liquid waste container 156 from the diluent holding container 155 through the fungus body detection flow path 173 by the pressure difference. Excitation light is irradiated to the fungus body detection flow path 173 in a direction perpendicular thereto, more preferably at an angle biased to the direction perpendicular thereto. Thus, dyed microorganisms emit fluorescence. The fluorescence is detected by the detection device 11. The peak wavelength of fluorescence of the all bacteria dyeing reagent 1531 is different from the peak wavelength of fluorescence of the killed bacteria dyeing reagent 1521. By detecting the fluorescence of the all bacteria dyeing reagent 1531, the total number of viable and killed bacteria can be detected. By detecting the fluorescence of the killed bacteria dyeing reagent 1521, the number of killed bacteria can be detected. The number of viable bacteria can be obtained by subtracting the number of killed bacteria from the total number of viable and killed bacteria.

Figure 2A:
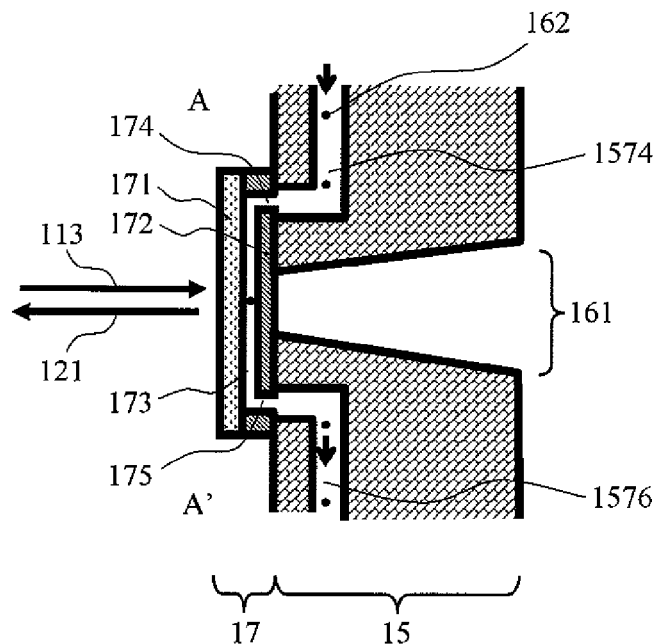
FIGS. 2A and 2B are views showing a configuration example of a fungus body detection unit of the microorganism testing chip of the present invention.
Figure 2B:
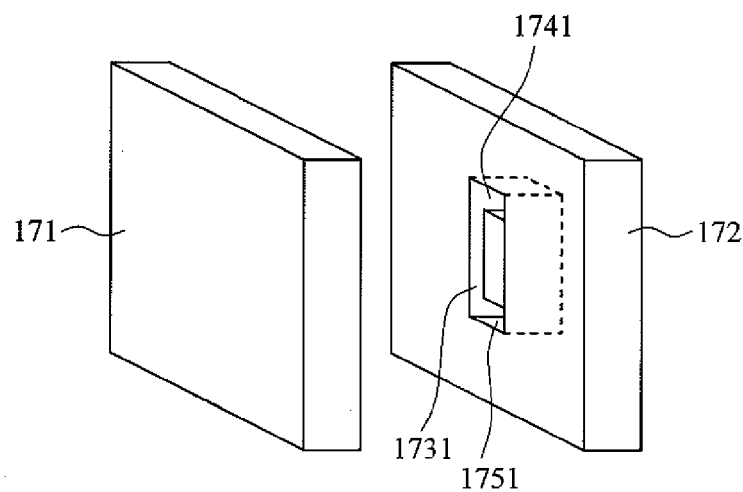

FIG. 2A is a cross-sectional view of a joint of the main body 15 and the fungus body detection unit 17. FIG. 2B is an exploded perspective view of the fungus body detection unit 17. The main body 15 and the fungus body detection unit 17 are fabricated in different processes and then joined together. First, a method of fabricating the fungus body detection unit 17 will be described. The fungus body detection unit 17 includes a cover member 171 and a flow path member 172. Both of these members are made of thin flat plates. The flow path member 172 has a groove 1731 formed therein, and further has through-holes 1741 and 1751 formed at respective ends of this groove 1731. The cover member 171 and the flow path member 172 are attached to each other so that the surface of the flow path member 172 which has the groove 1731 formed therein may be attached to the cover member 171. In this way, the fungus body detection unit 17 is formed. The groove 1731 of the flow path member 172 and the cover member 171 form the fungus body detection flow path 173. The through-holes 1741 and 1751 of the flow path member 172 form a fungus body detection flow path entrance 174 and a fungus body detection flow path exit 175, respectively.

On the other hand, the flow path 1574 between diluent holding container and fungus body detection flow path formed in the main body 15 changes the flow path direction thereof at the lower end thereof, and forms an opening in the surface of the main body 15. Similarly, the flow path 1576 between fungus body detection flow path and detection liquid waste container changes the flow path direction thereof at the upper end thereof, and forms an opening in the surface of the main body 15. The opening of the flow path 1574 between diluent holding container and fungus body detection flow path is connected to the fungus body detection flow path entrance 174, and the opening of the flow path 1576 between fungus body detection flow path and detection liquid waste container is connected to the fungus body detection flow path exit 175.

In the main body 15, a detection window frame portion 161 is formed. The detection window frame portion 161 is a through-hole or a pass-through groove. The detection window frame portion 161 is formed between the opening of the flow path 1574 between diluent holding container and fungus body detection flow path and the opening of the flow path 1576 between fungus body detection flow path and detection liquid waste container. After the fungus body detection unit 17 is fabricated, the fungus body detection unit 17 is mounted on the main body 15. As shown in FIG. 2A, the fungus body detection unit 17 is mounted so that the fungus body detection flow path 173 may be located on the detection window frame portion 161 of the main body 15.

Dyed fungus bodies 162 flow through the flow path 1574 between diluent holding container and fungus body detection flow path, the fungus body detection flow path entrance 174, the fungus body detection flow path 173, the fungus body detection flow path exit 175, and the flow path 1576 between fungus body detection flow path and detection liquid waste container in this order. Excitation light 113 incident on the fungus body detection flow path 173 is irradiated to the fungus bodies 162 flowing through the fungus body detection flow path 173. This causes the fungus bodies 162 to emit fluorescence 121 and to be detected by the detection device 11 (FIG. 3).

According to this example, the detection window frame portion 161, which is a through-hole or a pass-through groove, of the main body 15 is provided behind the fungus body detection flow path 173. Accordingly, the excitation light 113 is irradiated only to the fungus body detection unit 17 and not to the main body 15. Reflected light and self-fluorescence from the main body 15 which would cause an increase of background light are thus not generated. The cross section of the through-hole forming the detection window frame portion 161 preferably increases along the emission direction of the excitation light 113 so that the excitation light 113 which has passed through the fungus body detection flow path 173 may not be irradiated to the main body 15.

In the example shown in FIG. 2A, the central axis of the fungus body detection flow path 173 is biased with respect to the central axes of the flow path 1574 between diluent holding container and fungus body detection flow path and the flow path 1576 between fungus body detection flow path and detection liquid waste container. That is, the fungus body detection flow path 173 is not disposed in line with the flow path 1574 between diluent holding container and fungus body detection flow path and the flow path 1576 between fungus body detection flow path and detection liquid waste container. However, the fungus body detection flow path 173 may be disposed in line with the flow path 1574 between diluent holding container and fungus body detection flow path and the flow path 1576 between fungus body detection flow path and detection liquid waste container. In this case, the fungus body detection flow path 173 is connected directly to the flow path 1574 between diluent holding container and fungus body detection flow path and the flow path 1576 between fungus body detection flow path and detection liquid waste container.

The thickness of the cover member 171 is 0.01 μm to 1 mm. The thickness of the flow path member 172 is 0.01 μm to 1 mm. The cross-sectional shape of the fungus body detection flow path 173 is a square, a rectangle, or a trapezoid. The larger the cross section size of the fungus body detection flow path 173, the smaller the pressure loss. However, the cross section size of the fungus body detection flow path 173 is preferably smaller in order to flow microorganisms one by one. One side of the cross section of the fungus body detection flow path 173 is preferably 1 μm to 1 mm, and the length thereof is preferably 0.01 mm to 10 mm. The optical axis of the excitation light which is irradiated to the fungus body detection flow path 173 is perpendicular to the direction vector of the fungus body detection flow path 173.

The material for the fungus body detection unit 17 will be described. The microorganism testing chip 10 is disposable. That is, the fungus body detection unit 17 is discarded together with the main body 15 after use. For this reason, materials for use in the fungus body detection unit 17 must be inexpensive. Materials for use in the fungus body detection unit 17 need to be excellent in optical characteristics so as to be suitable for fluorescence measurement. That is, it is desirable that the materials have low self-fluorescence and be excellent in optical transparency, profile irregularity, and refractive index. The intensity of self-fluorescence emitted by the fungus body detection unit 17 itself is preferably significantly smaller than the intensity of fluorescence from fungus bodies in order not to inhibit the detection of the fluorescence from the fungus bodies.

In the case where the surface of the fungus body detection unit 17 is curved, uneven, or the like, the intensity of the excitation light 113 irradiated to the fungus body detection flow path 173 fluctuates due to the refraction of light or diffused reflection at the surface. Thus, the intensity of detected fluorescence also fluctuates, and measurement precision is lowered. Accordingly, the surface of the fungus body detection unit 17 preferably has desired flatness. The fungus body detection unit 17 preferably has flatness in which irregularities are 0.1 mm or less.

In consideration of the above-described conditions, possible materials for use in the fungus body detection unit 17 include glass, quartz, polymethacrylic acid methyl ester (PMMA), polydimethylsiloxane (PDMS), cyclo olefin polymer (COP), polyethylene terephthalate, poly carbonate, and the like. The fungus body detection unit 17 is formed from at least one material selected from these materials. The fungus body detection unit 17 is preferably formed from the same material as the main body 15. At least, the flow path member 172 is formed from the same material as the main body 15.

While the cover member 171 is a simple flat plate, the flow path member 172 is a flat plate having a groove and through-holes formed therein. Accordingly, the flow path member 172 is formed from an easily micromachinable material of low processing-cost. Glass and quartz are excellent in optical characteristics, but are not easily micromachinable. That is, the micromachining of glass or quartz requires a high processing cost.

Accordingly, the cover member 171 may be formed from glass or quartz, and the flow path member 172 may be formed from polymethacrylic acid methyl ester, polydimethylsiloxane, cyclo olefin polymer, polyethylene terephthalate, or poly carbonate. The flow path member 172 may preferably be formed from polydimethylsiloxane. In this case, the cover member 171 and the flow path member 172 are joined to each other by utilizing the self-adhesiveness of polydimethylsiloxane.

The intensity of self-fluorescence of the fungus body detection unit 17 depends not only on the material of the fungus body detection unit 17 but also on the thickness thereof. The intensity of the self-fluorescence can be reduced by reducing the thickness of the fungus body detection unit 17. The smaller the thickness of the fungus body detection unit 17, the smaller the intensity of the self-fluorescence emitted from the fungus body detection unit 17. However, if the thicknesses of the cover member 171 and the flow path member 172 are reduced, the fabrication thereof becomes difficult, and flatness becomes poor. To reduce the self-fluorescence intensity while maintaining necessary flatness without inhibiting the detection of fluorescence of fungus bodies, the thicknesses of these components need to be limited to certain ranges.

The intensities of self-fluorescence of glass, quartz, and polydimethylsiloxane are approximately equal. In the case where the cover member 171 is fabricated from glass or quartz, the thickness thereof is preferably in the range of 0.05 mm to 1 mm both inclusive. In the case where the flow path member 172 is fabricated from polydimethylsiloxane, the thickness thereof is preferably in the range of 0.1 mm to 1 mm both inclusive.

Alternatively, the cover member 171 and the flow path member 172 may be fabricated from cyclo olefin polymer, polymethacrylic acid methyl ester, polyethylene terephthalate, or poly carbonate. In this case, the intensity of the self-fluorescence per unit volume is three times larger than that in the case where the cover member 171 is fabricated from glass or quartz and where the flow path member 172 is fabricated from polydimethylsiloxane. Accordingly, the thicknesses of the cover member 171 and the flow path member 172 are preferably in the range of 0.01 mm to 0.3 mm both inclusive.

FIG. 3 is a configuration diagram of the microorganism testing device 1 of the present invention. The microorganism testing device 1 includes the microorganism testing chip 10 including the fungus body detection unit 17, an X-Y stage 125 for moving the microorganism testing chip 10 in X and Y directions, the detection device 11 which irradiates with the excitation light the fungus body detection unit 17 of the microorganism testing chip 10 and which detects fluorescence therefrom, and the pressure supply device 14 for supplying gas having a predetermined pressure to the microorganism testing chip 10. A system device 18 and an output device 19 are connected to the microorganism testing device 1. The microorganism testing chip 10 has been described with reference to FIG. 1. The X-Y stage 125 holds the microorganism testing chip 10, and positions the microorganism testing chip 10 by moving the microorganism testing chip 10 in the X and Y directions in response to a command signal from the system device 18. As shown in FIG. 3, an X axis and a Y axis are set in the horizontal plane. The X axis is perpendicular to the excitation light which is irradiated to the fungus body detection flow path 173 of the fungus body detection unit 17, and the Y axis is parallel to the excitation light.

The pressure supply device 14 includes a cylinder 141 with a pressure adjuster. Air, an inert gas, or the like at high pressure is encapsulated in the cylinder 141. The cylinder 141 is connected to the ventilation ports 1591-1596 (FIG. 1) of the microorganism testing chip 10 by chip connection pipes 1441-1446. To the chip connection pipes 1441-1446, valves 1421-1426 are provided, respectively. By opening or closing the valves 1421-1426, gas having a predetermined pressure is supplied to the containers of the microorganism testing chip 10, or the containers of the microorganism testing chip 10 are opened to the atmosphere. In this way, a specimen and reagents are transported in the microorganism testing chip 10 as described with reference to FIG. 1.

The detection device 11 includes an excitation light source 111, an excitation light-fluorescence separation dichroic mirror 112, an objective lens 114, a bandpass filter 117, a condenser lens 118, a pinhole 119, and an optical detector 120. The excitation light-fluorescence separation dichroic mirror 112 has the function of reflecting the excitation light 113 and allowing fluorescence to pass therethrough. That is, the excitation light-fluorescence separation dichroic mirror 112 reflects light with wavelengths near the wavelength of the excitation light 113, and allows light with wavelengths near the wavelength of the fluorescence to pass therethrough. The excitation light source 111, the excitation light-fluorescence separation dichroic mirror 112, and the objective lens 114 are disposed so that the optical axis of the excitation light 113 may be aligned with the central axis of the objective lens 114. This causes the excitation light 113 to be condensed at the focal point of a lens system including the objective lens 114 and the condenser lens 118.

When the positioning is performed, the positioning reagent 1541 is caused to flow into the fungus body detection flow path 173. When the number of fungus bodies is measured, a specimen is caused to flow into the fungus body detection flow path 173.

The excitation light 113 outputted from the excitation light source 111 is reflected by the excitation light-fluorescence separation dichroic mirror 112, condensed by the objective lens 114, and irradiated to the fungus body detection flow path 173. The fluorescence 121 from microorganisms or the positioning reagent 1541 passing through the fungus body detection flow path 173 of the fungus body detection unit 17 is converted into parallel light by the objective lens 114, passes through the excitation light-fluorescence separation dichroic mirror 112 and the bandpass filter 117, is condensed by the condenser lens 118, passes through the pinhole 119, and reaches the optical detector 120. The pinhole 119 functions as a spatial filter for cutting stray light. An electrical signal from the detection device 11 is sent to the system device 18. The system device 18 processes the electrical signal and outputs an obtained measurement result to the output device 19.

Figure 4A:
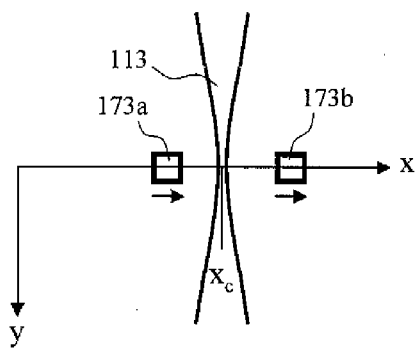
FIGS. 4A and 4B are schematic diagrams for explaining X-direction positioning of the microorganism testing device of the present invention.
Figure 4B:
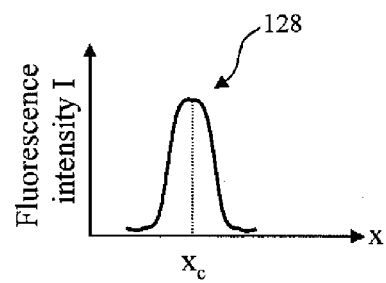
Figure 5A:
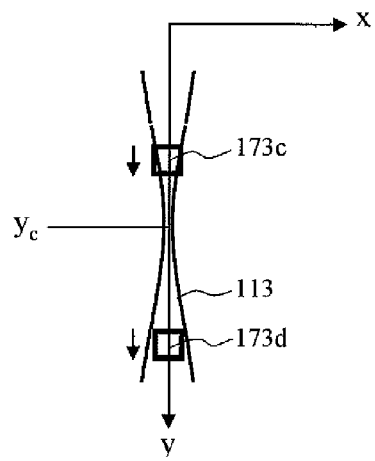
FIGS. 5A and 5B are schematic diagrams for explaining Y-direction positioning of the microorganism testing device of the present invention.

With reference to FIGS. 4 and 5, a method of positioning the fungus body detection flow path 173 will be described. The Y axis is set parallel to the optical axis of the excitation light 113 which is irradiated to the fungus body detection flow path 173, and the X axis is set perpendicular to the optical axis of the excitation light 113. FIGS. 4A and 5A schematically show the positions of the fungus body detection flow path 173 and the excitation light 113 when the fungus body detection unit 17 is sectioned by a plane parallel to the XY plane.

With reference to FIGS. 4A and 4B, an X-direction positioning method of the fungus body detection flow path 173 will be described. The positioning reagent 1541 is caused to flow into the fungus body detection flow path 173, and the microorganism testing chip 10 is moved in the X direction using the X-Y stage 125. FIG. 4A shows the X-direction position 173a of the fungus body detection flow path 173 before being moved and the X-direction position 173b of the fungus body detection flow path 173 after being moved. FIG. 4B shows an example of a graph 128 showing the relationship between the X-direction position of the fungus body detection flow path 173 and the fluorescence intensity I detected by the detection device 11 (FIG. 3). When the fungus body detection flow path 173 crosses the optical axis of the excitation light 113, the fluorescence intensity I becomes the maximum Accordingly, the X-direction position is preferably set using the X-Y stage 125 so that the fluorescence intensity I may become the maximum.

Figure 5B:
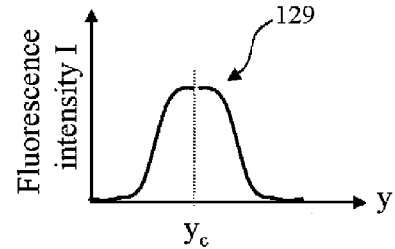

With reference to FIGS. 5A and 5B, a Y-direction positioning method of the fungus body detection flow path 173 will be described. The positioning reagent 1541 is caused to flow into the fungus body detection flow path 173, and the microorganism testing chip 10 is moved in the Y direction using the X-Y stage 125. FIG. 5A shows the Y-direction position 173c of the fungus body detection flow path 173 before being moved and the Y-direction position 173d of the fungus body detection flow path 173 after being moved. FIG. 5B shows an example of a graph 129 showing the relationship between the Y-direction position of the fungus body detection flow path 173 and the fluorescence intensity I detected by the detection device 11 (FIG. 3). When the fungus body detection flow path 173 crosses the optical axis of the excitation light 113, the fluorescence intensity I becomes the maximum. Accordingly, the Y-direction position is preferably set using the X-Y stage 125 so that the fluorescence intensity I may become the maximum.

Figure 6:
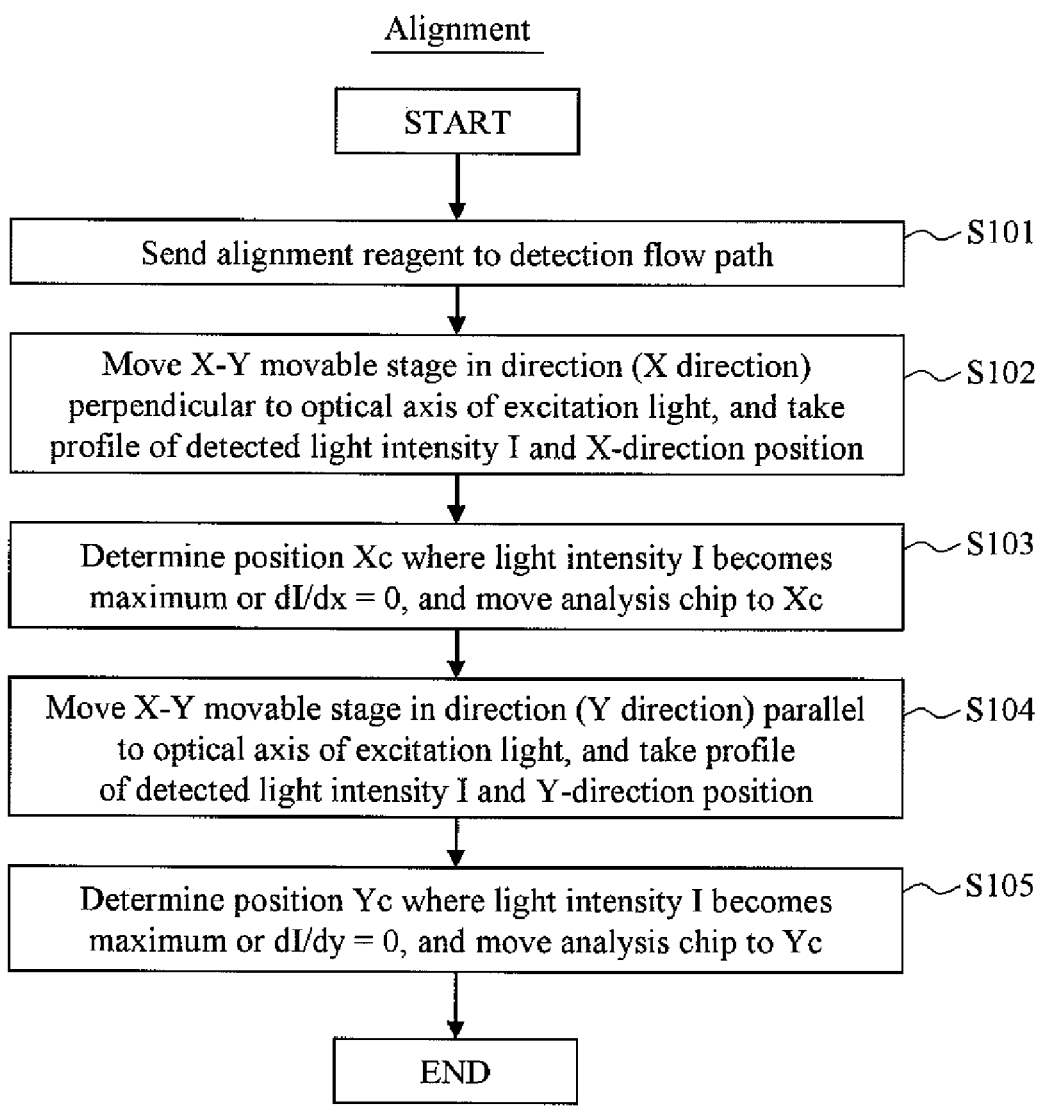
FIG. 6 is a view showing a procedure for positioning the microorganism testing chip of the microorganism testing device of the present invention.

With reference to FIG. 6, a procedure of positioning the microorganism testing chip 10, i.e., positioning the fungus body detection flow path 173, will be described. In step 5101, the microorganism testing chip 10 is mounted on the X-Y stage 125, and the positioning reagent 1541 is caused to flow into the fungus body detection flow path 173. As the positioning reagent 1541, for example, PI (wavelength peak: 532 nm) may be used. In step 5102, the microorganism testing chip 10 is moved in a direction perpendicular to the optical axis of the excitation light 113 using the X-Y stage 125. That is, as shown in FIG. 4A, the microorganism testing chip 10 is moved in the X direction. At the same time, as shown in FIG. 4B, the relationship between the X-direction position and the profile of the fluorescence intensity I detected by the detection device 11 is acquired. This profile is stored in the system device 18 (FIG. 3). In step S103, the position (X=Xc) where the fluorescence intensity I becomes the maximum or the position where the primary differential of the fluorescence intensity I with respect to the X direction becomes zero is determined. In this way, the X-direction position is obtained. The microorganism testing chip 10 is moved to that position.

Next, in step S104, the microorganism testing chip 10 is moved in a direction parallel to the optical axis of the excitation light 113 using the X-Y stage 125. That is, as shown in FIG. 5A, the microorganism testing chip 10 is moved in the Y direction. At the same time, as shown in FIG. 5B, the relationship between the Y-direction position and the profile of the fluorescence intensity I detected by the detection device 11 is acquired. This profile is stored in the system device 18

(FIG. 3). In step 5105, the position (Y=Y c) where the fluorescence intensity I becomes the maximum or the position where the primary differential of the fluorescence intensity I with respect to the Y direction becomes zero is determined. Steps S102 and S103 concern with X-direction positioning, and steps S104 and S105 concern with Y-direction positioning. Repeating the X-direction positioning and the Y-direction positioning enables high-precision positioning.

Figure 7:
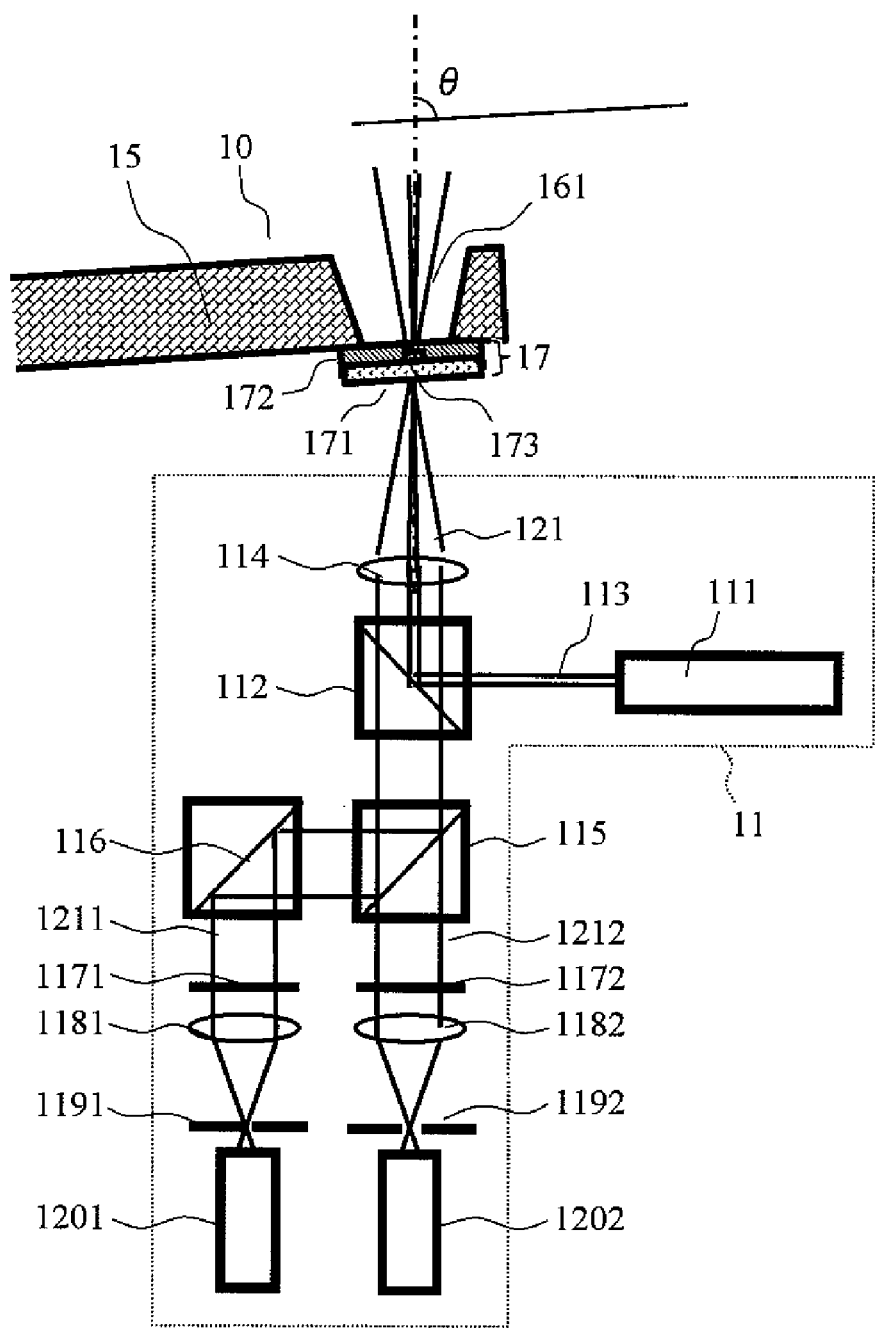
FIG. 7 is a view showing a configuration example of a detection device in the microorganism testing device of the present invention.

With reference to FIG. 7, a configuration example of a detection device of a microorganism testing device according to the present invention will be described. The detection device 11 of this example is suitable for measuring the number of viable bacteria in a specimen taken from a food. That is, in the detection device of this example, the number of viable bacteria and the number of killed bacteria are determined. The optical system of the detection device may differ depending on the excitation and fluorescence spectra of fluorochromes. Here, a description will be made of the case where PI (having an excitation wavelength peak at 532 nm and a fluorescence wavelength peak at 615 nm) is used as a killed bacteria dyeing reagent and where LDS751 (having an excitation wavelength peak at 541 nm and a fluorescence wavelength peak at 710 nm) is used as an all bacteria dyeing reagent. The optical system of the detection device in this example is configured so as to be suitable for the case where two kinds of fluorochromes are used.

The detection device 11 includes the excitation light source 111 (wavelength 532 nm); the excitation light-fluorescence separation dichroic mirror 112 which reflects the excitation light 113 and which allows fluorescence emitted from fungus bodies to pass therethrough; the objective lens 114 which condenses the fluorescence emitted from microorganisms passing through the fungus body detection flow path 173 to convert the fluorescence into parallel light; a fluorescence separation dichroic mirror 115 which reflects light with a wavelength of 610 nm or less and which allows light with a wavelength of 610 nm or more to pass therethrough; a mirror 116; a short wavelength bandpass filter 1171 which allows only light with wavelengths near 610 nm to pass therethrough; a long wavelength bandpass filter 1172 which allows light with wavelengths near 710 nm to pass therethrough; a short wavelength condenser lens 1181 and a long wavelength condenser lens 1182 for focusing parallel light; a short wavelength pinhole 1191 and a long wavelength pinhole 1192 to be used as spatial filters for cutting stray light; a short wavelength optical detector 1201 for detecting light which has passed through the short wavelength bandpass filter 1171; and a long wavelength optical detector 1202 for detecting light which has passed through the long wavelength bandpass filter 1172.

A laser is used as the excitation light source 111, and photomultipliers are used as the short wavelength optical detector 1201 and the long wavelength optical detector 1202. It is assumed that the positioning of the fungus body detection flow path 173 of the microorganism testing chip 10 has been completed as described above. The fungus body detection flow path 173 of the microorganism testing chip 10 is disposed at the position of the focal point of the objective lens 114.

The excitation light (wavelength: 532 nm) outputted from the excitation light source 111 is reflected by the excitation light-fluorescence separation dichroic mirror 112 to be irradiated to the fungus body detection flow path 173. In this way, PI and LDS751 which have dyed microorganisms flowing through the fungus body detection flow path 173 are excited. Fluorescence 1211 from the killed bacteria dyeing reagent PI (central wavelength of PI: 610 nm) and fluorescence 1212 from the all bacteria dyeing reagent LDS751 (central wavelength: 710 nm) enter the objective lens 114. The fluorescence 1211 from the killed bacteria dyeing reagent PI is reflected by the fluorescence separation dichroic mirror 115, and the fluorescence 1212 from the all bacteria dyeing reagent LDS751 passes through the fluorescence separation dichroic mirror 115. Thus, the fluorescence emitted from the two dyes can be separated based on the difference in wavelength. The fluorescence 1211 from the killed bacteria dyeing reagent PI passes through the short wavelength bandpass filter 1171, is condensed by the short wavelength condenser lens 1181, passes through the short wavelength pinhole 1191, and enters the short wavelength optical detector 1201. The fluorescence 1212 from the all bacteria dyeing reagent LDS751 passes through the long wavelength bandpass filter 1172, is condensed by the long wavelength condenser lens 1182, passes through the long wavelength pinhole 1192, and enters the long wavelength optical detector 1202.

The fluorescence detected by the short wavelength optical detector 1201 and the fluorescence detected by the long wavelength optical detector 1202 are respectively converted into electrical signals, and the electrical signals are sent to the system device 18 (FIG. 3). The system device 18 processes the electrical signals sent from the short wavelength optical detector 1201 and the long wavelength optical detector 1202, and outputs information on the number of microorganisms as a test result to the output device 19 (FIG. 3). The number of killed bacteria is obtained from the output of the short wavelength optical detector 1201, and the number of all bacteria is obtained from the output of the long wavelength optical detector 1202. The number of viable bacteria is obtained by subtracting the number of killed bacteria from the number of all bacteria.

Part of the excitation light 113 from the excitation light source 111 may be reflected by the surface of the fungus body detection unit 17 to return to the detection device 11. To prevent this phenomenon, in this example, the optical axis of the excitation light 113 is preferably not parallel to the normal vector of the fungus body detection unit 17. That is, the angle α between the normal vector of the fungus body detection unit 17 and the optical axis of the excitation light 113 is preferably in the range of 10° to 20°. As shown in FIG. 7, the angle between the surface of the fungus body detection unit 17 and the optical axis of the excitation light 113 is denoted by θ. The sum θ+α is 90°. The angle θ is less than 90 degrees and set so that the total reflection of the excitation light 113 may not occur at the surface of the fungus body detection unit 17. The angle θ may be in the range of 80° to 70°. It should be noted that though the fungus body detection unit 17 is inclined so that the normal vector of the fungus body detection unit 17 may not be parallel to the optical axis of the excitation light 113, the excitation light is irradiated to the fungus body detection flow path 173 in the direction perpendicular thereto.

Figure 8:
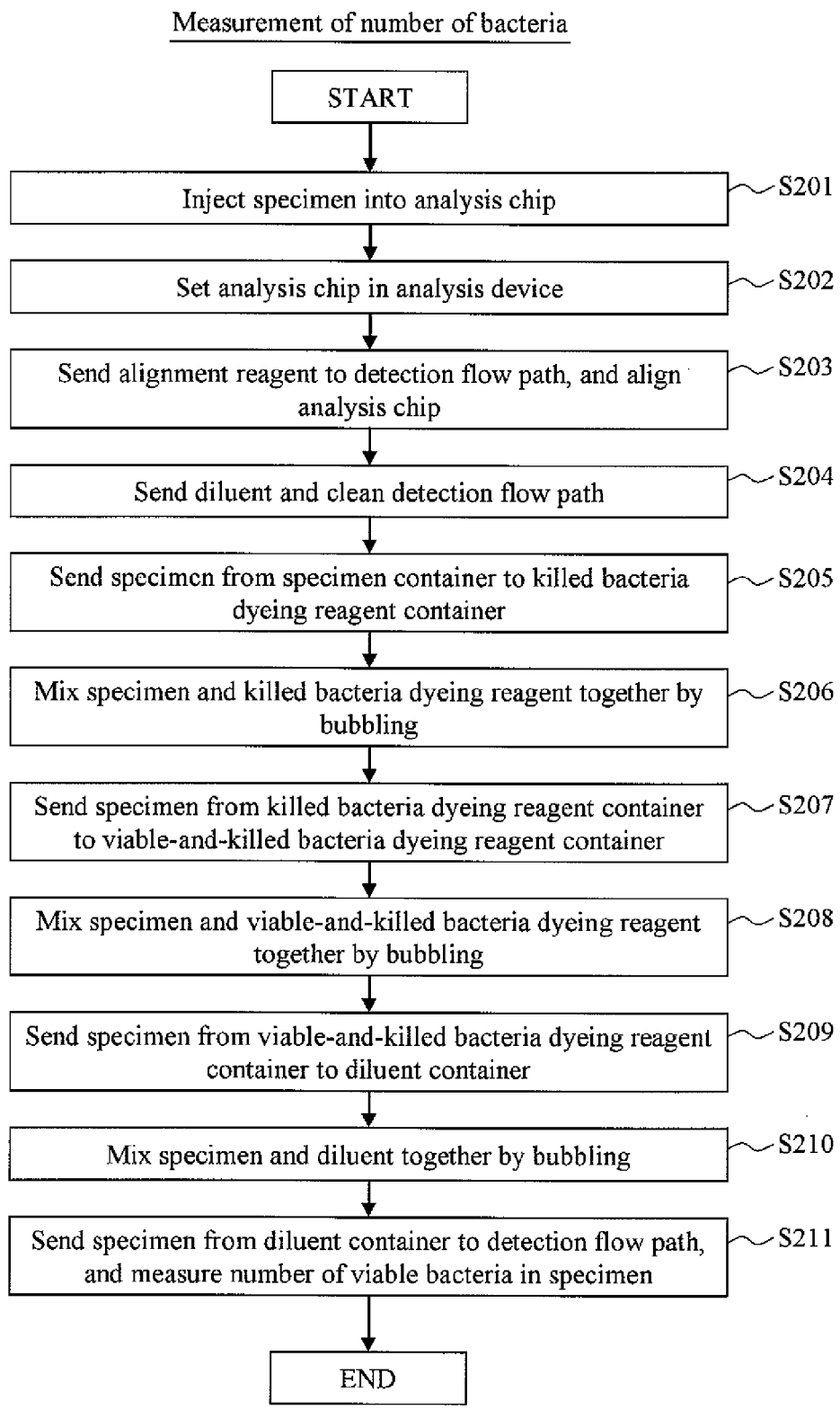
FIG. 8 is a view showing a procedure for microorganism testing in the microorganism testing device of the present invention.

With reference to FIGS. 8 and 1, a procedure for measuring the number of viable bacteria in a specimen taken from a food using the microorganism testing chip 10 of the present invention will be described. The killed bacteria dyeing reagent 1521, the all bacteria dyeing reagent 1531, and the positioning reagent 1541 are encapsulated in the microorganism testing chip 10 beforehand. The diluent 1551 is injected into the diluent holding container 155 before testing. In step S201, the specimen 1511 is injected into the specimen container 151 from the ventilation port 1591. The specimen 1511 is obtained by stomaching a food to be inspected after adding physiological salt solution which is ten times by mass relative to the food to be inspected. In step S202, the microorganism testing chip 10 is mounted on the X-Y stage 125 of the microorganism testing device. In step S203, the positioning of the microorganism testing chip, i.e., the positioning of the fungus body detection flow path 173, is performed. The positioning is performed by flowing the positioning reagent 1541 into the fungus body detection flow path 173 as described with reference to FIG. 6. In step S204, the diluent 1551 is caused to flow into the fungus body detection flow path 173 to wash out the positioning reagent 1541 adhering to the flow path.

Steps S205 to S211 concern with a process for measuring the number of viable bacteria in the specimen. In step S205, the specimen 1511 is caused to flow from the specimen container 151 through the food residue removing portion 160 into the killed bacteria dyeing reagent holding container 152. In step S206, the specimen 1511 and the killed bacteria dyeing reagent 1531 are mixed together by stirring. Killed bacteria in the specimen 1511 are dyed with the killed bacteria dyeing reagent 1521, but viable bacteria in the specimen 1511 are not dyed. In step S207, the liquid mixture of the specimen 1511 and the killed bacteria dyeing reagent 1521 is caused to flow into the all bacteria dyeing reagent holding container 153. In step S208, the liquid mixture of the specimen 1511 and the killed bacteria dyeing reagent 1521 is mixed with the all bacteria dyeing reagent 1531 by stirring. In step S209, the liquid mixture of the specimen 1511, the killed bacteria dyeing reagent 1521, and the all bacteria dyeing reagent 1531 is caused to flow into the diluent holding container 155. In step S210, the liquid mixture of the specimen 1511, the killed bacteria dyeing reagent 1521, and the all bacteria dyeing reagent 1531 is mixed with the diluent 1551 by stirring. The addition of the diluent 1551 reduces the concentration of uncombined dye contained in the liquid mixture. The reduction of the concentration of uncombined dye reduces the intensity of fluorescence emitted by uncombined dye which causes noise at the time of detection. In step S211, the liquid mixture of the specimen 1511, the killed bacteria dyeing reagent 1521, the all bacteria dyeing reagent 1531, and the diluent 1551 is caused to flow into the fungus body detection flow path 173. The excitation light is irradiated to the fungus body detection flow path 173 in a direction perpendicular thereto.

It should be noted, however, that the normal vector of the fungus body detection unit 17 is preferably not parallel to the optical axis of the excitation light 113. This allows dyed microorganisms flowing through the fungus body detection flow path 173 to emit fluorescence. The fluorescence is detected by the detection device 11. By detecting the fluorescence of the all bacteria dyeing reagent 1531, the total number of viable and killed bacteria can be detected. By detecting the fluorescence of the killed bacteria dyeing reagent 1521, the number of killed bacteria can be detected. The number of viable bacteria can be obtained from the difference between the foregoing numbers.

While an example of the present invention has been described above, the present invention is not limited to the above-described example. It will be readily appreciated by those skilled in the art that various modifications can be made within the scope of the invention described in the appended claims.

EXPLANATION OF REFERENCE NUMERALS

1 . . . microorganism testing device
10 . . . microorganism testing chip
11 . . . detection device
14 . . . pressure supply device
15 . . . main body
17 . . . fungus body detection unit
18 . . . system device
19 . . . output device
111 . . . excitation light source
112 . . . excitation light-fluorescence separation dichroic mirror
113 . . . excitation light
114 . . . objective lens
115 . . . fluorescence separation dichroic mirror
116 . . . mirror
117 . . . bandpass filter
118 . . . condenser lens
119 . . . pinhole
120 . . . optical detector
121 . . . fluorescence
125 . . . X-Y stage
127 relationship between X-direction position and output value
128 . . . relationship between Y-direction position and output value
151 . . . specimen container
152 . . . killed bacteria dyeing reagent holding container
153 . . . all bacteria dyeing reagent holding container
154 . . . positioning reagent holding container
155 . . . diluent holding container
156 . . . detection liquid waste container
157 . . . solution flow path
158 . . . air flow path
159 . . . ventilation port
160 . . . food residue removing portion
161 . . . detection window frame portion
162 . . . fungus body
171 . . . cover member
172 . . . flow path member
173 . . . fungus body detection flow path
174 . . . fungus body detection flow path entrance
175 . . . fungus body detection flow path exit

What is claimed is:
1. A microorganism testing chip comprising:
a main body; and
a fungus body detection unit mounted on the main body, wherein
the main body includes:
a specimen container;
a dyeing reagent holding container; and
a detection liquid waste container,
the specimen container, the dyeing reagent holding container, the fungus body detection unit, and the detection liquid waste container are connected by flow paths, and
a solution is moved between two of the containers by a pressure difference between the two containers, wherein
the main body further includes a detection window frame portion which is any one of a through-hole or a pass-through groove,
the fungus body detection unit is disposed to cover the detection window frame portion,
the fungus body detection unit includes a fungus body detection flow path connected to the flow paths provided in the main body,
the fungus body detection unit includes a cover member and a flow path member,
the flow path member has a groove, and
the groove of the flow path member serves as the fungus body detection flow path by attaching the cover member and the flow path member to each other, wherein the cover member forms a front side of the fungus body detection flow path and the flow path member forms a back side of the fungus body detection flow path, and wherein the detection window frame portion is provided behind the back side of the fungus body detection flow path.

2. The microorganism testing chip according to claim 1, wherein the cover member is formed from any one of a glass plate and a quartz plate having a thickness of 0.05 mm to 1 mm both inclusive, and the flow path member is formed from a polydimethylsiloxane plate having a thickness of 0.1 mm to 1 mm both inclusive.

3. The microorganism testing chip according to claim 1, wherein each of the cover member and the flow path member is formed from a plate of any one of cyclo olefin polymer, polymethacrylic acid methyl ester, and poly carbonate, the plate having a thickness of 0.01 mm to 0.3 mm both inclusive.

4. The microorganism testing chip according to claim 1, wherein the main body is made of at least one of materials selected from the group consisting of polypropylene, polystyrene, polyethylene terephthalate, poly carbonate, acrylonitrile butadiene styrene resin, and polymethacrylic acid methyl ester.

5. The microorganism testing chip according to claim 1, wherein the main body and the flow path member are made of the same material.

6. The microorganism testing chip according to claim 1, wherein the fungus body detection flow path is configured such that excitation light is incident the front side of the fungus body detection flow path.

7. A microorganism testing device comprising:
a microorganism testing chip including a main body and a fungus body detection unit mounted on the main body;
an X-Y stage for moving the microorganism testing chip in X and Y directions;
a detection device which irradiates with excitation light the fungus body detection unit of the microorganism testing chip and detects fluorescence from the fungus body detection unit; and
a pressure supply device for supplying gas having a predetermined pressure to the microorganism testing chip, wherein
the main body includes:
a specimen container;
a dyeing reagent holding container; and
a detection liquid waste container,
the specimen container, the dyeing reagent holding container, the fungus body detection unit, and the detection liquid waste container are connected by flow paths and also connected to the pressure supply device, and
a solution is moved between two of the containers by a pressure difference between the two containers, wherein
the main body further includes a detection window frame portion which is any one of a through-hole or a pass-through groove,
the fungus body detection unit is disposed to cover the detection window frame portion,
the fungus body detection unit includes a fungus body detection flow path connected to the flow paths provided in the main body,
the fungus body detection unit includes a cover member and a flow path member,
the flow path member has a groove, and the groove of the flow path member serves as the fungus body detection flow path by attaching the cover member and the flow path member to each other, wherein the cover member forms a front side of the fungus body detection flow path and the flow path member forms a back side of the fungus body detection flow path, and wherein the detection window frame portion is provided behind the back side of the fungus body detection flow path.

8. The microorganism testing device according to claim 7, wherein the angle α between the normal vector of an incident surface of the fungus body detection unit and an optical axis of the excitation light is 10° to 20°.

9. The microorganism testing device according to claim 7, wherein the excitation light is made incident on the fungus body detection flow path of the fungus body detection unit in a direction perpendicular to the fungus body detection flow path.

10. The microorganism testing device according to claim 7, wherein the cover member is formed from any one of a glass plate and a quartz plate having a thickness of 0.05 mm to 1 mm both inclusive, and the flow path member is formed from a polydimethylsiloxane plate having a thickness of 0.1 mm to 1 mm both inclusive.

11. The microorganism testing device according to claim 7, wherein each of the cover member and the flow path member is formed from a plate of any one of cyclo olefin polymer, polymethacrylic acid methyl ester, and poly carbonate, the plate having a thickness of 0.01 mm to 0.3 mm both inclusive.

12. The microorganism testing device according to claim 7, wherein the main body includes:
a killed bacteria dyeing reagent holding container; and
an all bacteria dyeing reagent holding container,
the detection device includes:
an excitation light source generating excitation light to be irradiated to the fungus body detection flow path;
a fluorescence separation optical system to separate fluorescence of the killed bacteria dyeing reagent and fluorescence of the all bacteria dyeing reagent from fluorescence emitted from microorganisms passing through the fungus body detection flow path;
a first detector which detects the fluorescence of the killed bacteria dyeing reagent and obtains the number of killed bacteria; and
a second detector which detects the fluorescence of the all bacteria dyeing reagent and obtains the number of all bacteria,
the number of viable bacteria is determined based on the difference between the number of all bacteria obtained by the second detector and the number of killed bacteria obtained by the first detector.

13. The microorganism testing device according to claim 7, wherein the main body includes a positioning reagent holding container, and at the time of positioning the microorganism testing chip, the positioning reagent is caused to flow into the fungus body detection flow path, the microorganism testing chip is moved using the X-Y stage, and the position of the microorganism testing chip is set using the X-Y stage so that the intensity of fluorescence detected by the detection device becomes the maximum.

14. The microorganism testing device according to claim 7, wherein the fungus body detection flow path is configured such that the excitation light is incident the front side of the fungus body detection flow path.

15. A method of fabricating a microorganism testing chip including a main body and a fungus body detection unit mounted on the main body, the method comprising the steps of:
fabricating the main body which includes
a specimen container,
a dyeing reagent holding container, and
a detection liquid waste container, the specimen container, the dyeing reagent holding container, the fungus body detection unit, and the detection liquid waste container connected by flow paths, a solution moved between two of the containers by a pressure difference between the two containers;
providing in the main body a detection window frame portion which is any one of a through-hole or a pass-through groove;
fabricating the fungus body detection unit including a cover member and a flow path member; and
disposing the fungus body detection unit to cover the detection window frame portion and then attaching the fungus body detection unit to the main body,
wherein the step of fabricating the fungus body detection unit includes the steps of:
forming the cover member from a plate;
forming the flow path member by forming a groove in a plate; and
attaching the cover member and the flow path member to each other to fabricate the fungus body detection unit having a fungus body detection flow path,
wherein the cover member forms a front side of the fungus body detection flow path and the flow path member forms a back side of the fungus body detection flow path, and
wherein the detection window frame portion is provided behind the back side of the fungus body detection flow path.

16. The method of fabricating a microorganism testing chip according to claim 15, wherein
the cover member is formed from any one of a glass plate and a quartz plate having a thickness of 0.05 mm to 1 mm both inclusive, and
the flow path member is formed from a polydimethylsiloxane plate having a thickness of 0.1 mm to 1 mm both inclusive.

17. The method of fabricating a microorganism testing chip according to claim 15, wherein each of the cover member and the flow path member is formed from a plate of any one of cyclo olefin polymer, polymethacrylic acid methyl ester, and poly carbonate, the plate having a thickness of 0.01 mm to 0.3 mm both inclusive.

18. The method of fabricating a microorganism testing chip according to claim 15, wherein the fungus body detection flow path is formed such that excitation light is incident the front side of the fungus body detection flow path.

* * * * *